US00PP32293P2

(12) United States Plant Patent
Holtmaat

(10) Patent No.: US PP32,293 P2
(45) Date of Patent: Oct. 6, 2020

(54) ***ECHINACEA* PLANT NAMED 'SCARLET IBIS'**

(50) Latin Name: ***Echinacea* hybrid**
Varietal Denomination: Scarlet Ibis

(71) Applicant: AB-Kwekersrechten BV, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 16/501,673

(22) Filed: May 20, 2019

(30) Foreign Application Priority Data

Mar. 12, 2019 (QZ) ..... PBR 2019/0678

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./263.1, 428
See application file for complete search history.

(56) References Cited

PUBLICATIONS

AB cultivars website (https://www.ab-cultivars.com/?portfolio=echinacea-flamingo). retrieved Feb. 10, 2020. 6 pages. (Year: 2018).*
UPOV-PLUTO: Plant Variety Database, Oct. 2, 2020, citation for 'Flamingo'. (Year: 2020).*
The Seed House website (https://www.etsy.com/listing/593852734/echinacea-supreme-seeds-flamingo-deer). Retrived Feb. 10, 2020. 4 pages. (Year: 2020).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Echinacea* plant named 'Scarlet Ibis' that is characterized by its inflorescences with ray florets that are light orange in color with lighter colored tips and red bases, its strong flowering stems, and its abundant flowering in the first year after propagation.

2 Drawing Sheets

Botanical classification: *Echinacea* hybrid.
Variety denomination: 'Scarlet Ibis'.

BACKGROUND OF THE INVENTION

The present invention relates to a new and distinct cultivar of *Echinacea* of hybrid origin and will be referred to hereafter by its cultivar name 'Scarlet Ibis'. 'Scarlet Ibis' is an herbaceous perennial grown for landscape and container use.

The new invention arose from an ongoing controlled breeding program in Zuidwolde, The Netherlands. The objective of the breeding program is to develop cultivars of *Echinacea* with unique flower color and short, sturdy plant habits.

The Inventor discovered the new cultivar as a chance seedling in July of 2017 in a trial field that was planted with seeds collected from numerous cultivars and proprietary plants. The parent plants are therefore unknown.

Asexual propagation of the new cultivar was first accomplished under the direction of the Inventor by tissue culture using meristem tissue in March 2018 in Heerhugowaard, The Netherlands. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Scarlet Ibis' as unique cultivar of *Echinacea*.

1. 'Scarlet Ibis' exhibits inflorescences with ray florets that are light orange in color with lighter colored tips and red bases.
2. 'Scarlet Ibis' exhibits strong flowering stems.
3. 'Scarlet Ibis' exhibits abundant flowering in the first year after propagation.

'Scarlet Ibis' can be most closely compared to the *Echinacea* cultivars 'Julia' (U.S. Plant Pat. No. 24,629) and 'Cleopatra' (U.S. Plant Pat. No. 24,631). 'Julia' is similar to 'Scarlet Ibis' in having a short plant height and in foliage color. 'Julia' differs from 'Scarlet Ibis' in having a slightly smaller plant height, having stronger stems, and ray florets that are orange in color that lacks lighter colored tips and red bases. 'Cleopatra' is similar to 'Scarlet Ibis' in plant height and in having strong stems. 'Cleopatra' differs from 'Scarlet Ibis' in having slightly smaller inflorescences with ray florets that are yellow in color and in commencing bloom earlier in the season.

BRIEF DESCRIPTION OF THE DRAWINGS

The accompanying colored photographs illustrate the overall appearance and distinct characteristics of the new

*Echinacea*. The photographs were taken of ten-month-old plants of the new cultivar grown outdoors in a 15-cm container in Zuidwolde, The Netherlands.

Figure 1:
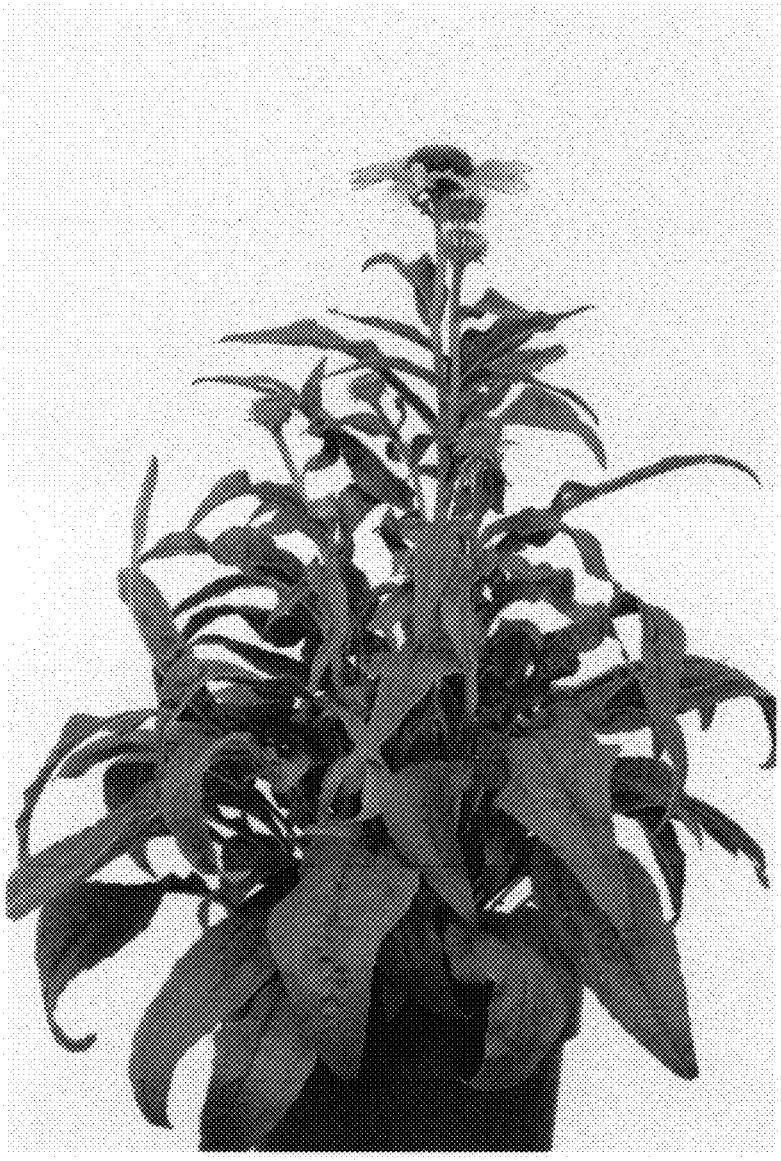

The photograph in FIG. 1 illustrates the overall habit and appearance of 'Scarlet Ibis' in bloom.

Figure 2:
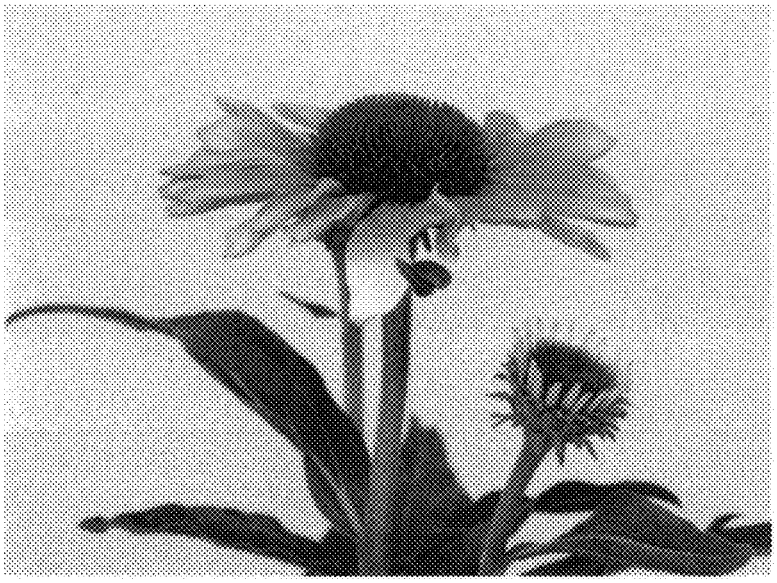

The photograph in FIG. 2 provides a close-up view of an inflorescence of 'Scarlet Ibis'.

Figure 3:
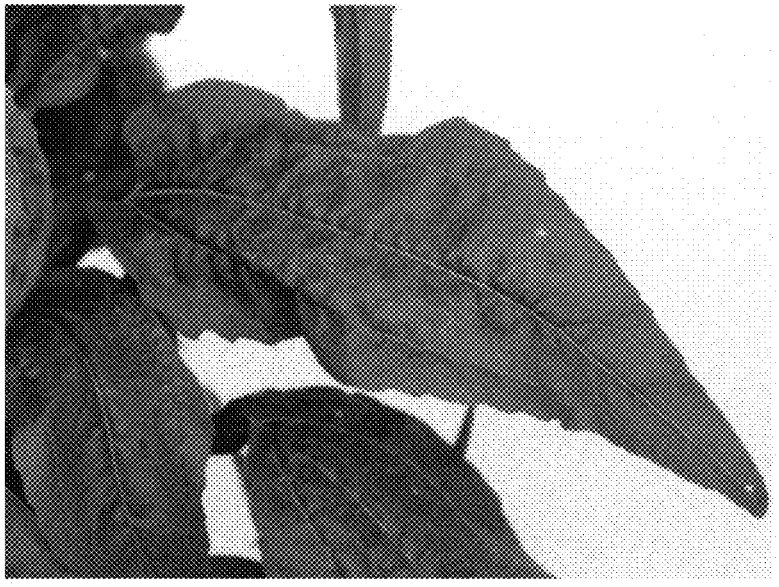

The photograph in FIG. 3 provides a close-up view of a leaf of 'Scarlet Ibis'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of ten-month-old plants of the new cultivar as grown outdoors in 15-cm containers in Zuidwolde, The Netherlands. The phenotype of the new cultivar may vary with variations in environmental, climatic, and cultural conditions, as it has not been tested under all possible environmental conditions. The color determination is in accordance with The 2015 RHS Colour Chart of The Royal Horticultural Society, London, England, except where general color terms of ordinary dictionary significance are used.

General description:

*Blooming period.*—Blooms for 10 weeks from early July to late September, in The Netherlands.

*Plant type.*—Herbaceous perennial.

*Plant habit.*—Compact, upright, broad ovate in shape.

*Height and spread.*—An average of 50 cm (including inflorescences) in height and 50 cm in spread as planted in the landscape.

*Hardiness.*—At least in U.S.D.A Zones 4 to 9.

*Diseases and pests.*—No susceptibility and resistance to diseases or pests has been observed.

*Root description.*—Fibrous and fine, 158D in color.

*Propagation.*—Tissue culture using meristem tissue.

*Growth rate.*—Moderate.

*Root development.*—Rooting occurs in about 10 weeks and a young rooted plant can be produced in about 3 months.

Stem description:

*Shape.*—Rounded.

*Stem color.*—144C and moderately marbled 144B.

*Stem size.*—An average of 30.2 cm in length, 7 mm in diameter.

*Stem strength.*—Very strong.

*Stem aspect.*—Primary branches grow in an average angle of 20° to vertical stems (0°=vertical).

*Stem surface.*—Slightly to moderately covered with very short strigose hairs an average of 0.3 mm in length and NN155D in color.

*Stem number.*—Average of 4 main branches (basal).

*Internode length.*—Average of 4.6 cm in length.

*Branching.*—Main flowering stem grows from base.

Foliage description:

*Leaf shape.*—Basal leaves narrow ovate, cauline leaves narrow ovate to lanceolate.

*Leaf division.*—Simple.

*Leaf base.*—Basal leaves and cauline leaves attenuate.

*Leaf apex.*—Basal leaves and cauline leaves narrow acute.

*Leaf venation.*—Pinnate, basal and cauline leaves; 143B in color on upper surface and 144B in color on lower surface.

*Leaf margin.*—Basal leaves and cauline leaves coarsely un-deeply dentate-crenate and slightly undulate.

*Leaf attachment.*—Petiolate.

*Leaf arrangement.*—Alternate.

*Leaf size.*—Basal leaves average of 21.0 cm in length and 8 cm in width, cauline leaves average of 16.7 cm in length and 4.7 cm in width.

*Leaf color.*—Basal and cauline leaves: young upper surface; 137B, young lower surface; 147B, mature upper surface; a color in between 139A and 147A, mature lower surface; a color in between 147B and 147A.

*Leaf surface.*—Basal and cauline leaves; upper surface very slightly glossy, rough to touch, moderately rugose, with short strigose hairs an average of 0.3 mm in length and too fine to measure color, lower surface matte, rough to touch, moderately rugose, with short strigose hairs an average of 0.3 mm in length and too fine to measure color.

*Petioles.*—V-shaped, basal leaves an average of 10.2 cm in length and 3 mm in diameter, cauline leaves an average of 3.7 cm in length and 3 mm in diameter, color upper surface 144B and 187B towards the proximal end and margined NN137B, color lower surface 144A and fading towards the proximal end to 187C to 187D, both surfaces smooth and glabrous, strong.

Flower description:

*Type.*—Terminal capitulum consisting of ray florets and disc florets.

*Capitulum number.*—An average of 4 per stem, 18 per plant.

*Lastingness of inflorescence.*—A few weeks, ray florets self-cleaning.

*Capitulum size.*—Matures to about 2.9 cm in height and 9.6 cm in diameter, disc diameter is an average of 3.9 cm.

*Inflorescence aspect.*—Held straight on top of peduncles.

*Fragrance.*—Moderately faint, sweet and pleasant.

*Involucral bracts or phyllary.*—Rotate, 64 arranged in 3 overlapping rows, average of 8 mm in length and 3 mm in width, cuneate base, acute apex, ovate to narrow ovate in shape, color upper surface 138A and darker towards the margins and top 137A, color lower surface 146A, upper surface texture; smooth, lower surface texture; matte with very short strigose hairs an average of 0.3 mm in length and too fine for color reading, margins are entire and moderately pubescent with very short strigose hairs an average of 0.3 mm in length and too fine for color reading.

*Inflorescence buds.*—Flattened globular in shape, immature ray florets tilted upward at an average angle of 45° to horizontal, an average of 2.5 cm in length and 4.3 cm in diameter, color 143A and 172A with immature ray florets 10C, matte surface.

*Peduncle.*—Strong, terminal is an average of 7.1 cm in length and 5 mm in diameter, secondary is 3.5 cm in length and 5 mm in diameter, aspect of terminal peduncles straight on top of main stem, aspect of secondary peduncles: 15° (0°=straight upright), 144C in color and moderately marbled with 144B, surface is slightly to moderately covered with very short strigose hairs; an average of 0.3 mm in length and NN155D in color.

*Ray Florets.*—Rotate around disc in 1 row, average of 26 (varying between 23 and 30) per inflorescence, obovate in shape, average of 3.8 cm in length and 1.4 cm in width, emarginate to praemorse apex, narrow cuneate base, entire margin, held at an average angle of 5° downward from horizontal, color; upper surface when opening 31B, fading towards tip to N170D and fading towards base to 54B, lower surface when opening 54C and fading towards the base to 146D, upper surface when fully open 25B to 25C and changing towards the tip to N170D and 150C and slightly fading towards the base to 54B to 54C, lower surface when fully open 54D and fading towards the base to 146D, surface texture; upper surface glabrous, matte and carinate, lower surface glabrous, slightly glossy and carinate.

*Disk flowers* (*bisexual*).—Numerous, average of 500, arranged spirally on disc, tubular, upright to outward aspect, apex is acute on upper 15% that is free, fused (tubular) base, entire margin, average of 1.0 cm in length and 3 mm in width, upper and lower surface textures are smooth, glabrous and glossy, color when opening and fully open upper and lower surface; apex 143A with very tip 183A, mid-section N170D, base 187D.

*Disk spines.*—Average of 500, acicular in shape, acute apex, attenuate base, glabrous and glossy surface, color is 187A and 42B and 23A at apex, 143B to 143C in mid region and 157D at base.

*Receptacle.*—Broad ovate in shape, an average of 1.2 cm in height and 1.4 cm in diameter, 155C in color.

Reproductive organs (present on disk florets only):

*Gynoecium.*—Pistil; average 1; 6 mm in length, style; 5 mm in length and 154D in color, stigma; unequal decurrent and a color between 187A and 203C in color, ovary; 157D in color.

*Androecium.*—Stamens; 5, filaments; 3.5 mm in length and N170D in color, anthers; linear in shape, average of 3.5 mm in length, 200A in color, pollen is moderate in quantity and 23A in color.

*Fruit/seed.*—No seed production has been observed to date.

It is claimed:

1. A new and distinct cultivar of *Echinacea* plant named 'Scarlet Ibis' as herein illustrated and described.

* * * * *